(12) United States Patent
Hsieh et al.

(10) Patent No.: US 8,834,932 B2
(45) Date of Patent: Sep. 16, 2014

(54) ANTICOAGULANT-CONJUGATED CARBON NANOCAPSULE, ANTITHROMBOTIC AGENT CONTAINING THEREOF

(71) Applicant: Industrial Technology Research Institute, Hsinchu (TW)

(72) Inventors: Patrick C. H. Hsieh, Tainan (TW); Alan C. L. Tang, Tainan (TW); Gan-Lin Hwang, Tainan (TW)

(73) Assignee: Industry Technology Research Institute, Hsinchu (TW)

( * ) Notice: Subject to any disclaimer, the term of this patent is extended or adjusted under 35 U.S.C. 154(b) by 0 days.

(21) Appl. No.: 13/669,830

(22) Filed: Nov. 6, 2012

(65) Prior Publication Data

US 2013/0156856 A1   Jun. 20, 2013

(30) Foreign Application Priority Data

Dec. 19, 2011   (TW) .............................. 100147057 A

(51) Int. Cl.
| | |
|---|---|
| *A61K 9/14* | (2006.01) |
| *B32B 5/16* | (2006.01) |
| *A61K 9/50* | (2006.01) |
| *C08B 37/00* | (2006.01) |
| *A61K 47/48* | (2006.01) |
| *B82Y 5/00* | (2011.01) |
| *B82B 1/00* | (2006.01) |

(52) U.S. Cl.
CPC ............... *A61K 9/50* (2013.01); *C08B 37/0075* (2013.01); *A61K 47/48869* (2013.01); *B82Y 5/00* (2013.01); *C08B 37/00* (2013.01); *B82B 1/00* (2013.01)
USPC .......................................... 424/489; 428/402

(58) Field of Classification Search
USPC ......... 977/702, 740, 742, 746, 810, 803, 805, 977/915, 803 K, 744, 745, 748, 753; 424/489; 428/402
See application file for complete search history.

(56) References Cited

U.S. PATENT DOCUMENTS

| | | | |
|---|---|---|---|
| 6,841,509 B1 * | 1/2005 | Hwang et al. ................ | 502/180 |
| 7,985,426 B1 | 7/2011 | Sung et al. | |
| 8,007,768 B1 | 8/2011 | Sung et al. | |
| 8,017,237 B2 | 9/2011 | Ludwig et al. | |
| 2004/0126303 A1 * | 7/2004 | Hwang ....................... | 423/447.2 |
| 2010/0316694 A1 | 12/2010 | Mousa et al. | |

FOREIGN PATENT DOCUMENTS

| | | |
|---|---|---|
| CN | 1563157 | 1/2005 |
| CN | 101361992 | 2/2009 |
| CN | 101491835 | 7/2009 |
| CN | 101962410 | 2/2011 |

(Continued)

OTHER PUBLICATIONS

Thermo Scientific, "Carbodiimide Crosslinker Chemistry" (piercenet.com/browse.cfm?fldID=F3305493-0FBC-93DA-2720-4412D198A9C9, last visit: Jul. 31, 2013).*

(Continued)

*Primary Examiner* — Ernst V Arnold
*Assistant Examiner* — Kyung Sook Chang
(74) *Attorney, Agent, or Firm* — Muncy, Geissler, Olds & Lowe, P.C.

(57) ABSTRACT

The embodiments provide a carbon nanocapsule conjugated with at least one of the anticoagulants on the surface and an antithrombotic drug containing the anticoagulant-conjugated carbon nanocapsule as an active ingredient. The anticoagulant-conjugated carbon nanocapsule has less cytotoxicity and good biocompatibility. A method for preparing the anticoagulant-conjugated carbon nanocapsule is also provided.

19 Claims, 23 Drawing Sheets

(56) References Cited

FOREIGN PATENT DOCUMENTS

| TW | 200410904 A | 7/2004 |
|---|---|---|
| TW | 200503833 A | 2/2005 |
| WO | WO2006061925 | 2/2009 |

OTHER PUBLICATIONS

Murugesan et al. "Blood compatible carbon nanotubes—Nano-based Neoproteoglycans", Langmuir, 2006, 22, pp. 3461-3463.*

Heparin-Coated Nanomaterials Go with the Flow by Heather Thompson (2006).*

Melissa M. Kemp et al. "Heparin-based Nanoparticles", WIREs Nanomedicine and Nanobiotechnology vol. 2, Jan./Feb. 2010, pp. 77-87.

Yuanqing Gu et al., "Functional Polymeric Hybrid Nanotubular Materials Derived from Natural Cellulose Substances", The Royal Society of Chemistry 2010J. Mater. Chem., 2010, 20, Apr. 5, 2010, pp. 10217-10223.

J. Myerson et al., "Thrombin-inhibiting Perfluorocarbon Nanoparticles Provide a Novel Strategy for the Treatment and Magnetic Resonance Imaging of Acute Thrombosis", Journal of Thrombosis and Haemostasis, 9, Apr. 14, 2011, pp. 1292-1300.

Chiung-Hung Chang et al. "Development of Novel Nanoparticles Shelled with Heparin for Berberine Delivery to Treat *Helicobacter pylori*", Acta Biomaterialia 7 (2011), Sep. 17, 2010, pp. 593-603.

Shuhua Bai et al. "Synthesis and Evaluation of Pegylated Dendrimeric Nanocarrier for Pulmonary Delivery of Low Molecular Weight Heparin", Pharmaceutical Research, vol. 26, No. 3, Mar. 2009, pp. 539-548.

Gao et al, "Covalent Immobilization of Proteins on Carbon Nanotubes Using the Cross-Linker 1-Ethyl-3-(3-dimethylaminopropyl)carbodiimide—a Critical Assessment," Bioconjugate Chemistry, 2008, pp. 1945-1948, vol. 19, No. 10.

Song et al, "Hierarchical Porous Core-Shell Carbon Nanoparticles," Chemistry of Materials, 2009, pp. 1524-1530, vol. 21.

Official Action issued on Aug. 29, 2013, by the Taiwanese Patent Office in correspoding TW Patent Application No. 100147057.

* cited by examiner

ANTICOAGULANT-CONJUGATED CARBON NANOCAPSULE, ANTITHROMBOTIC AGENT CONTAINING THEREOF

CROSS REFERENCE TO RELATED APPLICATIONS

This application claims the priority of Taiwan Patent Application No. 100147057, filed Dec. 19, 2011, which is incorporated herein by reference.

BACKGROUND

1. Technical Field

The technical field relates to an anticoagulant-conjugated carbon nanocapsule and antithrombotic agents.

2. Description of the Related Art

Anticoagulants refer to the agents for preventing blood clotting, primarily comprising vitamin K antagonists (coumarin derivatives) and heparin derivatives in clinics.

Warfarin is one of the vitamin K antagonists, clinically used for the treatment of prosthetic heart valves, atrial fibrillation and ischemic strokes (Kenichi A. et al., Blood coagulation: hemostasis and thrombin regulation, *Anesth Analg* 2009; 108:1433-46). However, due to genetic factors, diet or similar factors, it is usually difficult to keep wafarin at an effective concentration. In addition, wafarin may have side effects like bleeding in the gastrointestinal and urinary tracts, intracranial hemorrhage or complications after administration.

On the other side, heparin derivatives are effective on acute and chronic prevention of thrombosis. Although heparin derivatives have excellent anticoagulated effects, the use is limited due to its short half-life (about 30~90 minutes) after intravenous injection, unpredictable pharmacokinetics by subcutaneous administration, hypersensitivity and thrombocytopenia (Kenichi A. et al., Blood coagulation: hemostasis and thrombin regulation, *Anesth Analg* 2009; 108:143346). In addition, the efficacy of heparin may be reduced when the antithrombin activity is low, and the antithrombin activity decreases due to pregnancy, severe burn, hepatic dysfunction, nephritic syndrome, sepsis, and the use of estrogen or L-asparaginase (Kenichi A. et al., Blood coagulation: hemostasis and thrombin regulation, *Anesth Analg:* 2009; 108:1433-46).

SUMMARY

A detailed description is given in the following embodiments with reference to the accompanying drawings.

One embodiment of the invention provides a carbon nanocapsule conjugated with at least one of the anticoagulants.

Another embodiment of the invention provides an antithrombotic agent which contains a carbon nanocapsule conjugated with at least one of the anticoagulants as an active ingredient.

Another embodiment of the invention provides a method for preparing an anticoagulant-conjugated carbon nanocapsule. The method comprises functionalizing a surface of the carbon nanocapsule, mixing the said functionalized carbon nanocapsule with anticoagulants and isolating the anticoagulant-conjugated carbon nanocapsules.

BRIEF DESCRIPTION OF THE DRAWINGS

The disclosure can be more fully understood by reading the subsequent detailed description and examples with references made to the accompanying drawings, wherein:

FIGS. 2A~2F show the cytotoxicity of various carbon materials according to an exemplary embodiment, in which: FIG. 2A shows the effects of various carbon materials on the viability of fibroblast cells NIH/3T3 after 24 hours; FIG. 2B shows the effects of various carbon materials on the viability of Hela cells after 24 hours; FIG. 2C shows the effects of various carbon materials on the viability of stem cells hMSC after 24 hours; FIG. 2D shows the effects of various carbon materials on the viability of fibroblast cells NIH/3T3 after 48 hours; FIG. 2E shows the effects of various carbon materials on the viability of Hela cells after 48 hours; and FIG. 2F shows the effects of various carbon materials on the viability of stem cells hMSC after 48 hours.

FIGS. 3A~3D show the effects of various carbon materials on cell apoptosis according to an exemplary embodiment, in which: FIG. 3A shows the effects of various carbon materials on the apoptosis of fibroblast cells NIH/3T3 after 24 hours; FIG. 3B shows the effects of various carbon materials on the apoptosis of Hela cells after 24 hours; FIG. 3C shows the effects of various carbon materials on the apoptosis of fibroblast cells NIH/3T3 after 48 hours; and FIG. 3D shows the effects of various carbon materials on the apoptosis of Hela cells after 48 hours.

FIGS. 4A~4F show the effects of various carbon materials on the murine cumulative mortality according to an exemplary embodiment, in which: FIG. 4A shows the effect of PBS on the murine cumulative mortality; FIG. 4B shows the effect of PVA on the murine cumulative mortality; FIG. 4C shows the effect of CNCs on the murine cumulative mortality; FIG. 4D shows the effect of C60 on the murine cumulative mortality; FIG. 4E shows the effect of MWCNTs on the murine cumulative mortality; and FIG. 4F shows the effect of SWCNTs on the murine cumulative mortality. In these figures, the triangle refers to the high-dose group (50 µg/g), the circle refers to the group dosing 25 µg/g and the cross refers to the group dosing 12.5 µg/g (12 mice in each of the CNC-treated and C60-treated groups, and 11 mice in each of the PBS-treated, SWCNT-treated and MWCNT-treated groups). The triangle, circle and cross may overlap, indicating that the three groups show the same cumulative mortality at the same time.

FIGS. 5A~5B show the remaining of the carbon materials in the murine lung tissue according to an exemplary embodiment in which: FIG. 5A shows the murine lung tissue after intravenous injection of PBS, PVA, SWCNT, MWCNT, CNC and C60; and FIG. 5B shows the murine lung tissues of the FIG. 5A by histochemical straining.

FIGS. 6A~6B show the remaining of the carbon materials in the murine lung tissues according to an exemplary embodiment, in which: FIG. 6A shows the murine lung tissues after intravenous injection of PBS, PVA, SWCNTs, MWCNTs, CNCs and C60 by histochemical staining; and FIG. 6B shows the remaining amount of the carbon materials in the murine lung tissues of the FIG. 6A.

FIGS. 9A~9B show in vitro releases of the heparin-conjugated carbon nanocapsule according to an exemplary embodiment, in which: FIG. 9A shows a release of heparin in 0~24 hours; and FIG. 9B shows a release of heparin in 0~168 hours.

FIG. 10A shows the in vitro coagulation of carbon nanocapsules, heparin conjugated carbon nanocapsules, a mixture of carbon nanocapsules and heparins, and normal serum according to an exemplary embodiment.

FIG. 10B shows the ex viva coagulation of carbon nanocapsules, heparin-conjugated carbon nanocapsules, a mixture of carbon nanocapsules and heparins, and normal serum according to an exemplary embodiment.

DETAILED DESCRIPTION

Figure 1:
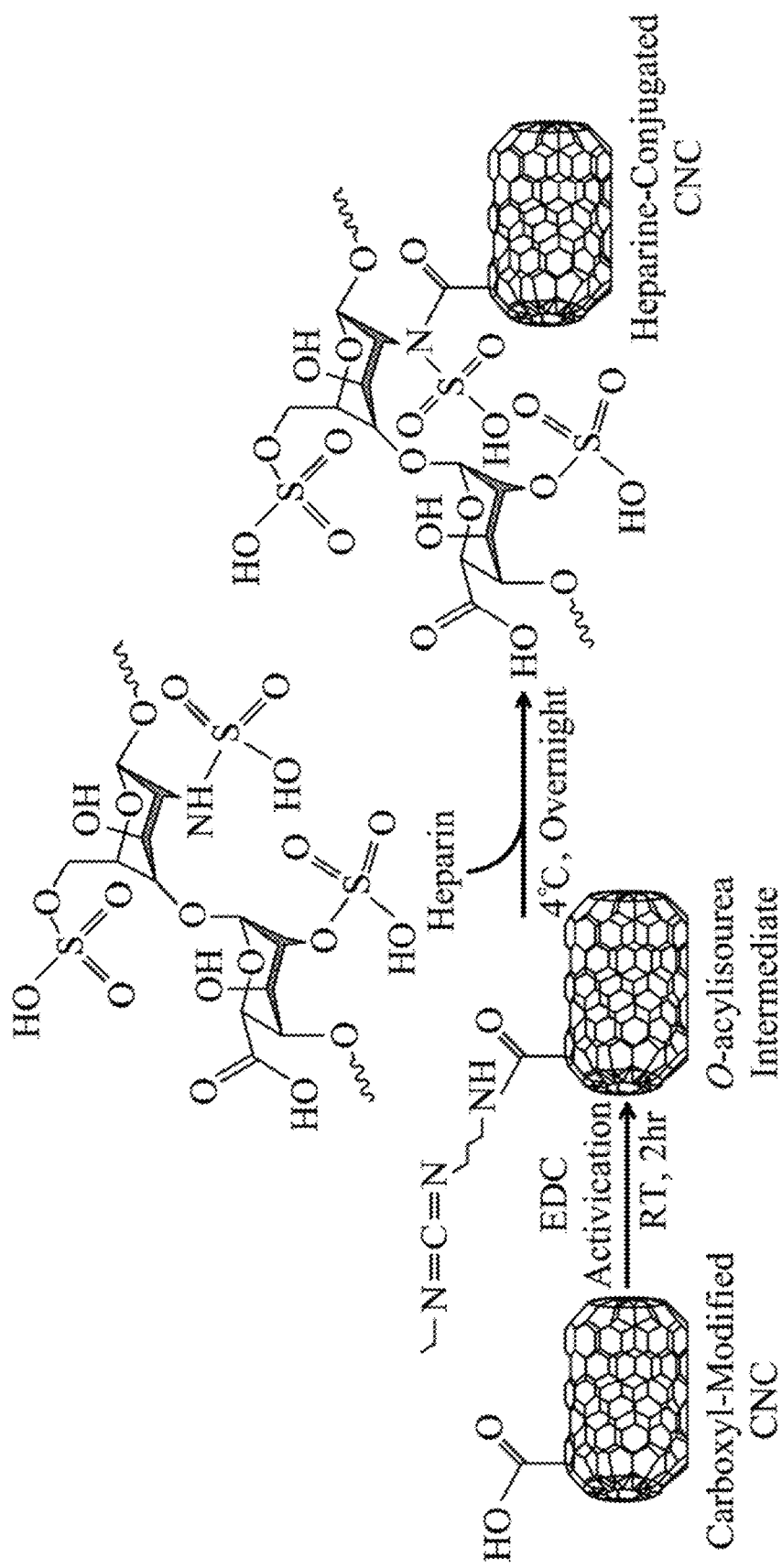
FIG. 1 shows the formation of the heparin-conjugated carbon nanocapsule according to an exemplary embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The carbon nanocapsule (CNC) according to embodiments of the invention is a polyhedral carbon cluster consisting of multiple graphite layers having a balls-within-a ball structure. According to embodiments of the invention, the carbon nanocapsule may be hollow or filled with metals, metal oxides, metal carbides or alloys thereof More specifically, the metal of the metals, metal oxides, metal carbides and alloys thereof may be selected from a group consisting of Sc, V, Cr, Fe, Co, Ni, Y, Zr, Mo, Ru, Pd, La, Ce, Pr, Nd, Gd, Tb, Dy, Ho, Er, Tm, Lu, Ta, Os, Ir, Pt, Au, Th and U, but it is not limited thereto. No matter if the carbon nanocapsule is hollow or metal-filled, the structure and features of the multiple graphite layers are unchanged. However, according to the features of the fillers, the carbon nanocapsule can be used for imaging, heat therapy or the like, and the dispersion of the carbon nanocapsules may be controlled by electromagnetism.

According to embodiments of the invention, the carbon nanocapsule may have an average diameter of about 1~100 nm, while it is about 3~60 nm in the case where the carbon nanocapsule is hollow and about 3~100 nm in the case where the carbon nanocapsule is metal-filled.

It has been well-known that single-wall carbon nanotubes (SWCNTs) and multiple-wall carbon nanotubes (MWCNTs) have the multiple graphite layer structure similar to carbon nanocapsules. However, concerning cytotoxicity and biocompatibility, SWCNTs and MWCNTs are not suitable for pharmaceutical uses. As shown in the following examples, carbon nanocapsules show lower cytotoxicity, good biocompatibility and higher body clearance in comparison with SWCNTs or MWCNTs. Accordingly, the carbon nanocapsule is considered an ideal pharmaceutical carrier.

The anticoagulant-conjugated carbon nanocapsule according to embodiments of the invention is characterized by the conjugation of the anti-coagulant of the surface of carbon nanocapsule. The anticoagulant refers to an active agent with a function against blood clotting (thrombosis). The anticoagulant may specifically comprise heparin, plasmin, serine protease, urokinase, streptokinase, warfarin, acenocoumarol, phenindione, a vitamin K antagonist, a tissue plasminogen activator or the like, but it is not limited thereto. In one example, heparin is selected as the anticoagulant and is conjugated to the surface of carbon naocapsules. In this example, the heparin-conjugated carbon nanocapsule is able to increase the local concentration of heparin in the body, preventing abnormal bleeding or complications induced by single administration of heparin as known in the conventional arts.

In embodiments of this invention, the use of carbon nanocapsules for a carrier carrying anticoagulants is novel. Because carbon nanocapsules are able to conjugate at least one of the anticoagulants on the surface, the anticoagulant-conjugated carbon nanocapsule according to the embodiments of the invention can elevate the local concentration of the anticoagulant at a specific region and lyse thrombi at the region. The anticoagulant-conjugated carbon nanocapsule according to the embodiments of the invention is conjugated with $1 \sim 10^5$ anticoagulants on the surface, but it is not limited thereto. Alternatively, the anticoagulant-conjugated carbon nanocapsule according to the embodiments of the invention may have a conjugation rate of 5~40%, or 20~30%, with the anticoagulants.

The anticoagulant-conjugated carbon nanocapsule according to the embodiments of the invention may be prepared by the following steps:

functionalizing a surface of the carbon nanocapsule;

mixing the surface-functionalized carbon nanocapsule with anticoagulants; and isolating the anticoagulant-conjugated carbon nanocapsules.

The step of functionalization of the surface refers to surface modification of the carbon nanocapsule to form a functional group on the surface of the carbon nanocapsule. The surface functionalization recited in embodiments of the invention is not specifically limited, which may depend on the species of anticoagulants or crosslinkers, or similar factors. In one example, the carbon nanocapsule is modified to have a carboxyl group (—COOH) (FIG. 1) on the surface. In this example, the carboxyl-modified carbon nanocapsule conjugates with the anticoagulant, heparin, via amide bond formation.

The surface functionalization according to embodiments of the invention may be performed by immerging carbon nanocapsules into appropriate solvents to modify the surface of the carbon nanocapsules. In one example, the surface of the carbon nanocapsule is modified to have a carboxyl group (—COOH) via immersion in an acidic solution. The acidic solution recited herein may comprise hydrochloric acid, sulfate acid or a mixture thereof. In the example, the acidic solution is preferably a mixed solution consisting of equal volumes of hydrochloride acid and sulfate acid.

In one embodiment of the invention, the method for preparing the carbon nanocapsule may further add crosslinkers in the step for linking the anticoagulant to the surface of the carbon nanocapsule. The crosslinker recited herein is not specifically limited, which may be the crosslinkers conventionally used for conjugation. In one example of the invention, the crosslinker may comprises 1-ethyl-3-(3-dimethylaminopropyl)carbodiimide (EDC) or N,N'-dicylcohexyl carbodiimide. In one example, the carboxyl-modified carbon nanocapsules form an O-acylisourea intermediate with EDCs which is then replaced with heparins to form heparin-conjugated carbon nanocapsules by formation of an amide bond (FIG. 1). In this example, N-hydroxysulfosuccinimide can be further added to accelerate EDC-mediated crosslinking.

According to embodiments of the invention, the anticoagulant-conjugated carbon nanocapsule is able to increase the anticoagulant concentration at a specific region because one carbon nanocapsule conjugates at least one of the anticoagulants. Therefore, the anticoagulant-conjugated carbon nanocapsule is able to lyse thrombi locally. Compared to the conventional anticoagulants which result in bleeding at untreated regions or capillary broken, the anticoagulant-conjugated carbon nanocapsule according to the invention can enhance the anticoagulation at the region being treated and avoid the risk of developing side effects. Thus, the anticoagulant-conjugated carbon nanocapsule according to the invention solves the long-lasting difficulties in the conventional art and can be a potent active ingredient of antithrombotic agents.

One embodiment of the invention provides an antithrombotic agent comprising the anticoagulant-conjugated carbon nanocapsule as an active ingredient. The antithrombotic agent according to embodiments of the invention may further comprise pharmaceutically acceptable carriers or additives. The pharmaceutically acceptable carriers or additives may comprise excipients, anti-oxidants, emulsifying agents, dispersing agents, bacteriostatic agents, flavors, pigments, buffers, solvents, pH modulators, surfactants or the like. The carriers or additives can be suitably adjusted according to the dosage forms and administration routes. The antithrombotic agent according to embodiments of the invention may be pellets, capsules, film-coated tablets, powders, suspensions or injections through oral, transdermal, intraperitoneal or intravenous administration. The dosage forms and administration routes are not limited, but it is administered intravenously. The anticoagulant-conjugated carbon nanocapsule and antithrombotic agent according to embodiments of the invention can be administered individually or with other drugs. The dosing amount may depend on the age, weight, health condition, disease and development or the affected region of the patient and be decided by the medical practitioner according to routine clinic practices.

The antithrombotic agent according to embodiments of the invention is able to prevent perioperative thrombus formation or treat cardiovascular diseases. The cardiovascular disease may comprise a stroke, acute coronary syndrome, atrial fibrillation, coronary occlusion, deep vein thrombosis or pulmonary embolism, but it is not limited thereto.

EXAMPLES

Example 1

Cytotoxicity of Carbon Materials

The cell lines MSC (Mouse mesenchymal stem cells, primary, from FVB bone marrow isolation, 5000 cells/cm$^2$, from ATCC), Hela (cell line, 5000 cells/cm$^2$) and NIH/3T3 (cell line, 5000 cells/cm$^2$) were prepared. Each cell line was added phosphate buffer saline (PBS), polyvinyl alcohol (PVA), single-wall carbon nanotubes (SWCNTs) in PVA, multiple-wall carbon nanotubes (MWCNTs) in PVA, carbon nanocapsules (CNCs) in PVA and carbon 60 (C60) in PVA (50 µg/ml, 100 µg/ml, 200 µg/ml), respectively and cultured for 48 hours. The CNC, in this and the following examples, was prepared according to U.S. Pat. No. 7,156,958, which is incorporated herein by references. Cell viability and apoptosis at 24 and 48 hours were recorded.

Figure 2A:
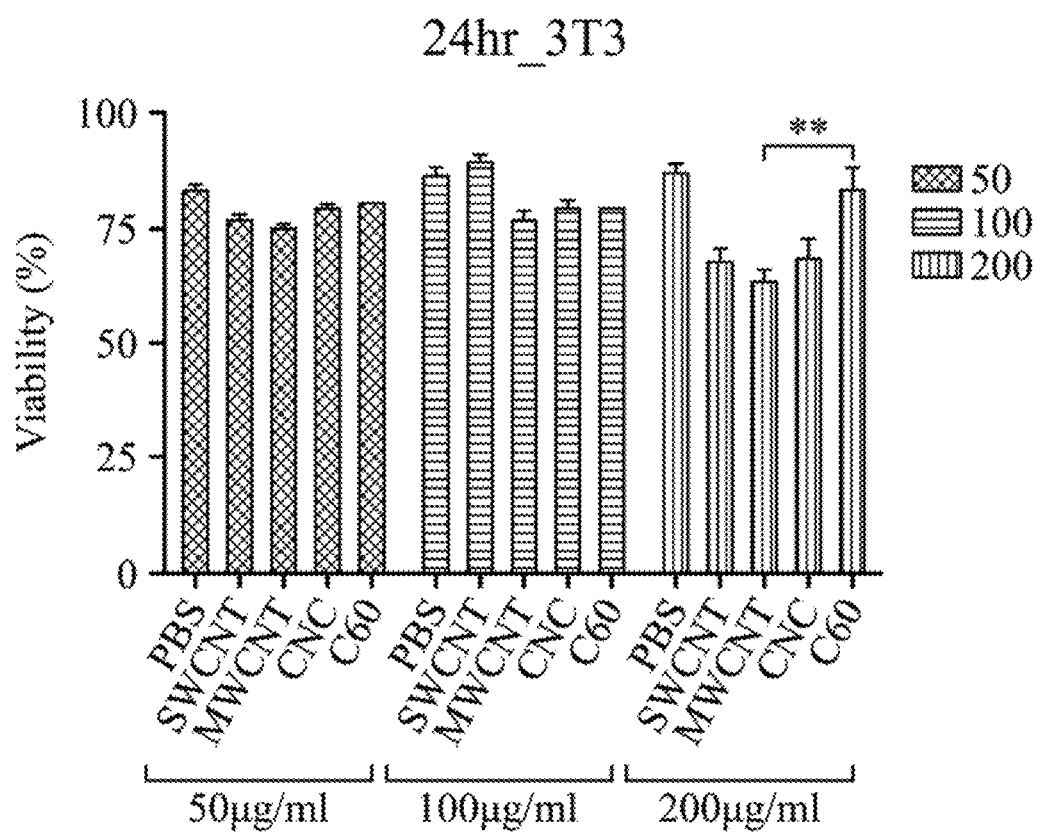
Figure 2B:
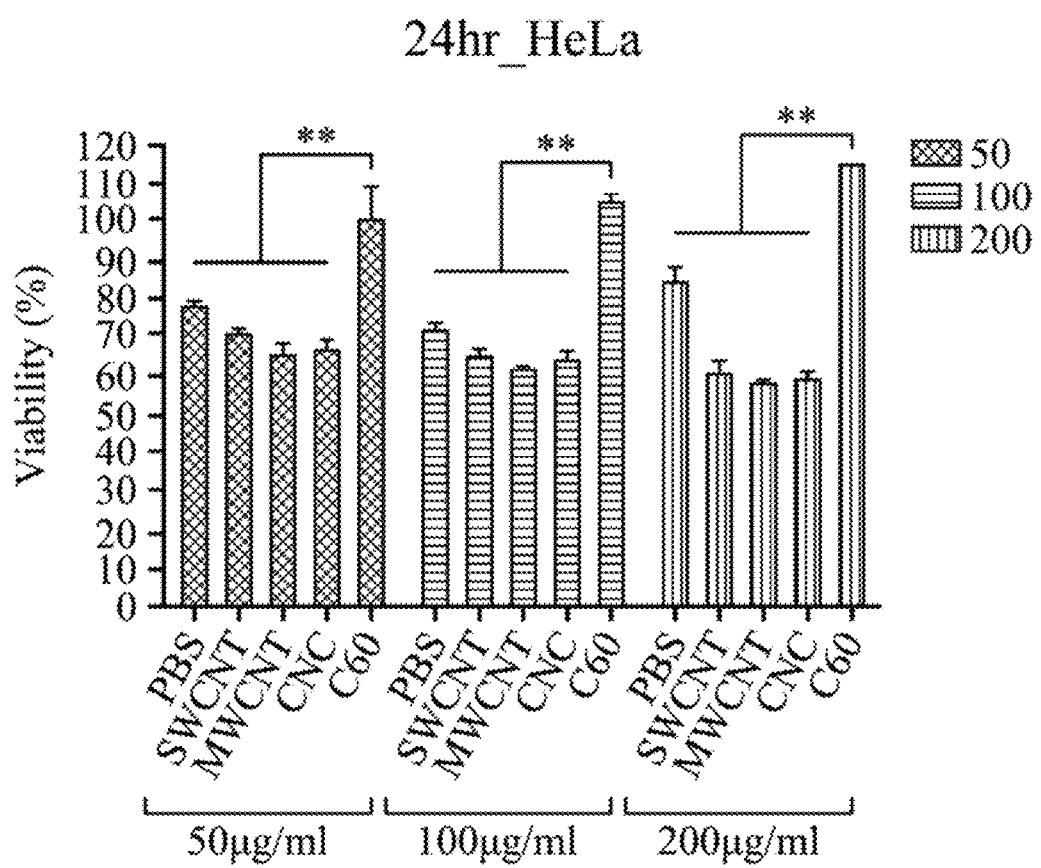
Figure 2C:
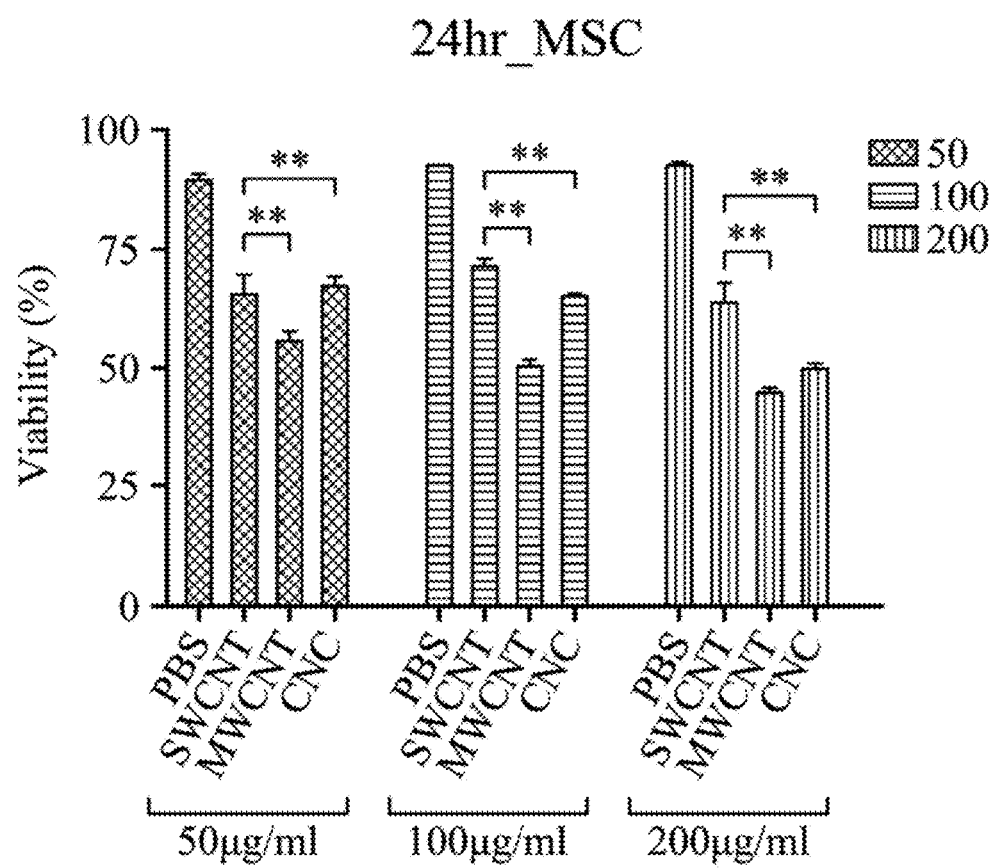
Figure 2D:
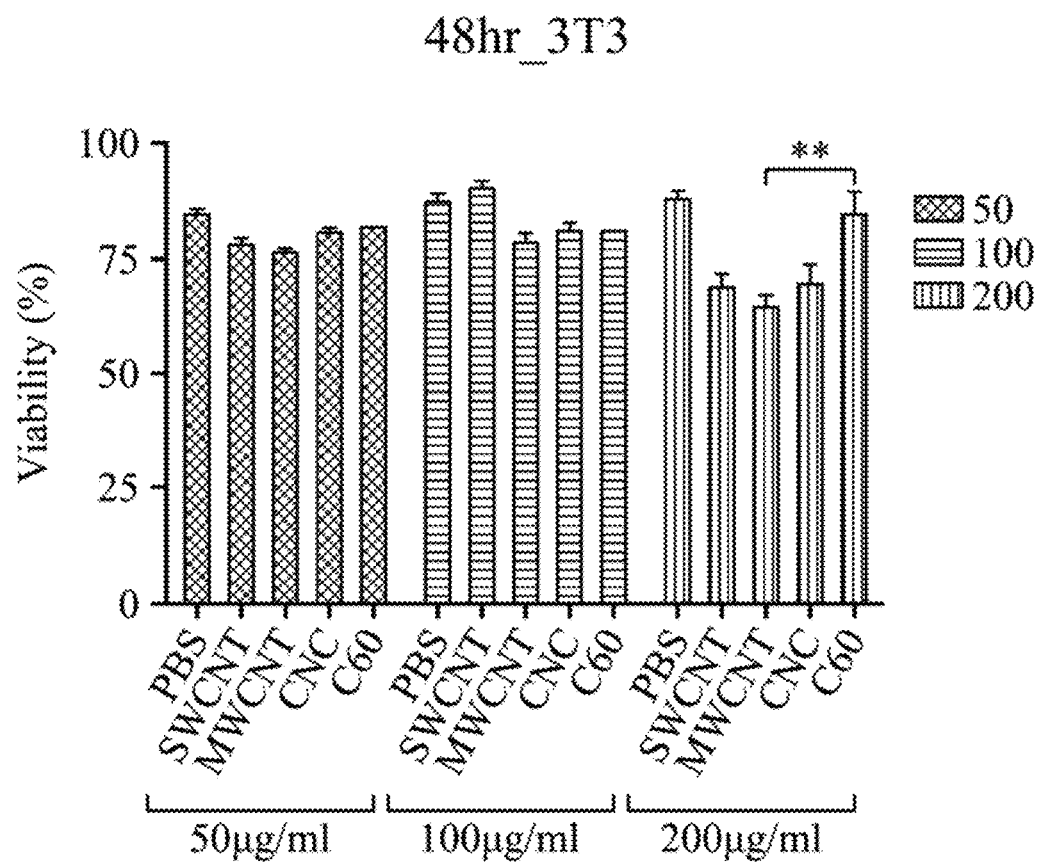
Figure 2E:
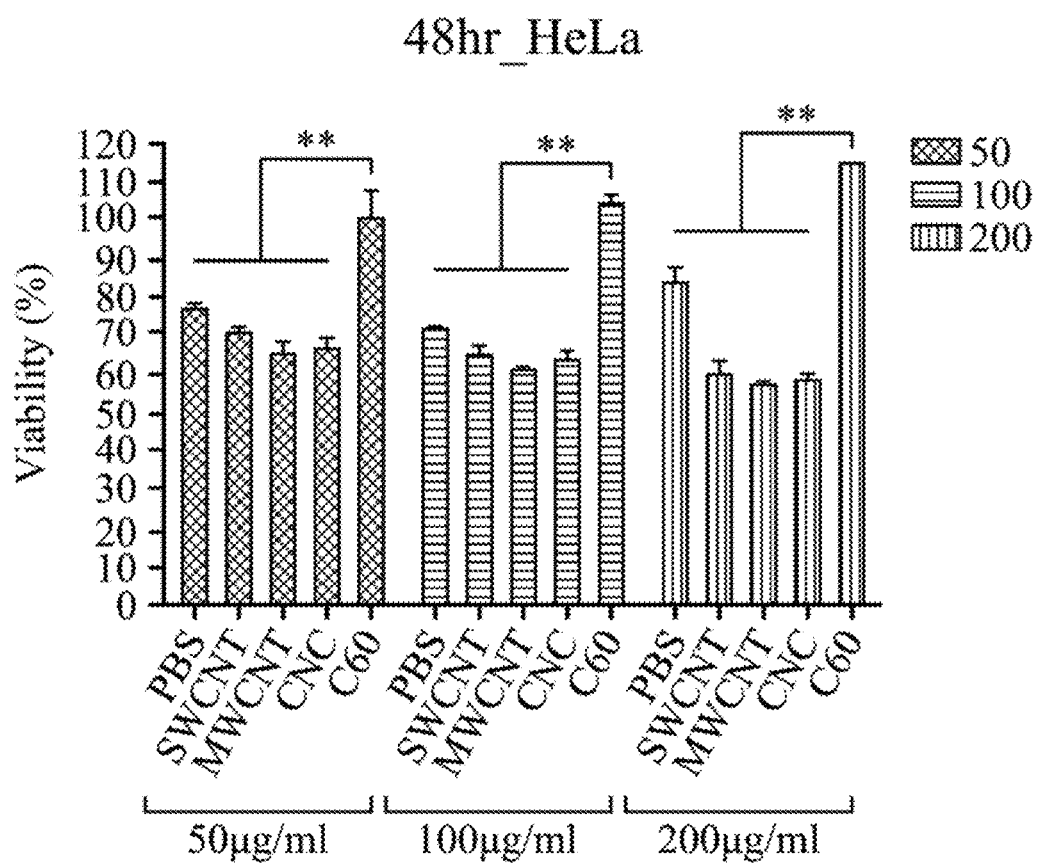
Figure 2F:
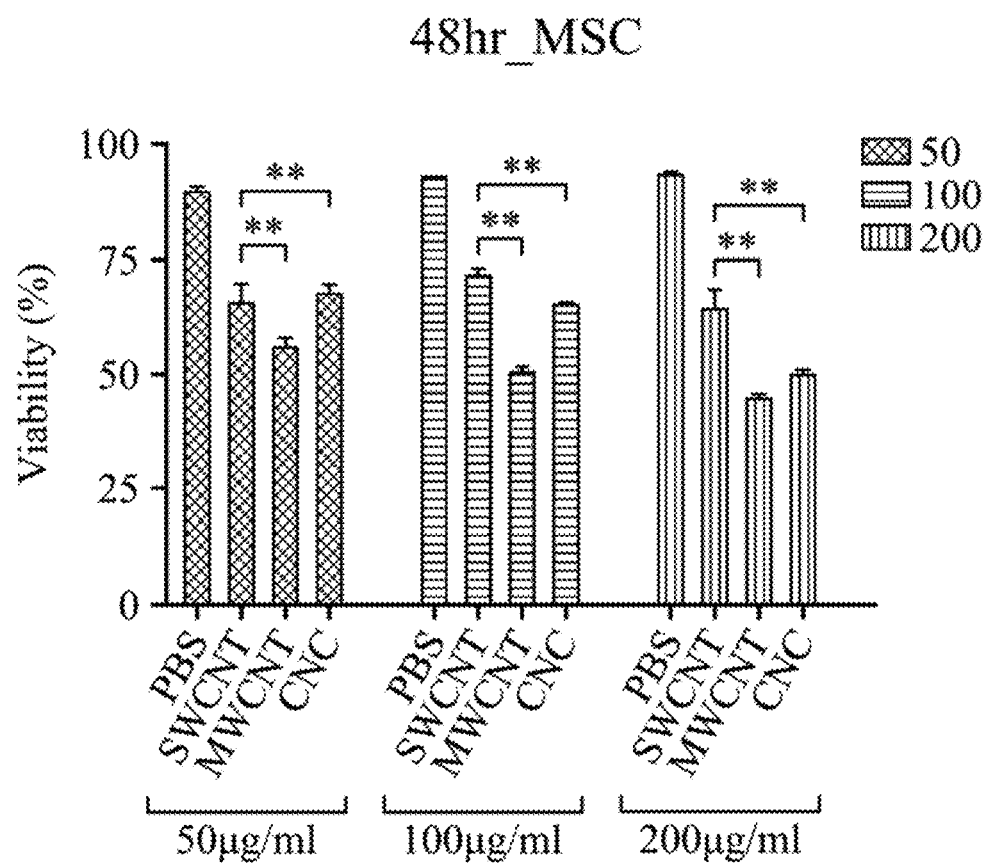

The cell viability is shown in FIGS. 2A~2E. Despite C60, all carbon materials in PVA caused gentle toxicity after 24 hour-culture (FIGS. 2A~2C). After 48 hour-culture, all carbon materials caused quite low cytotoxicity (FIGS. 2D~2E).

Figure 3A:
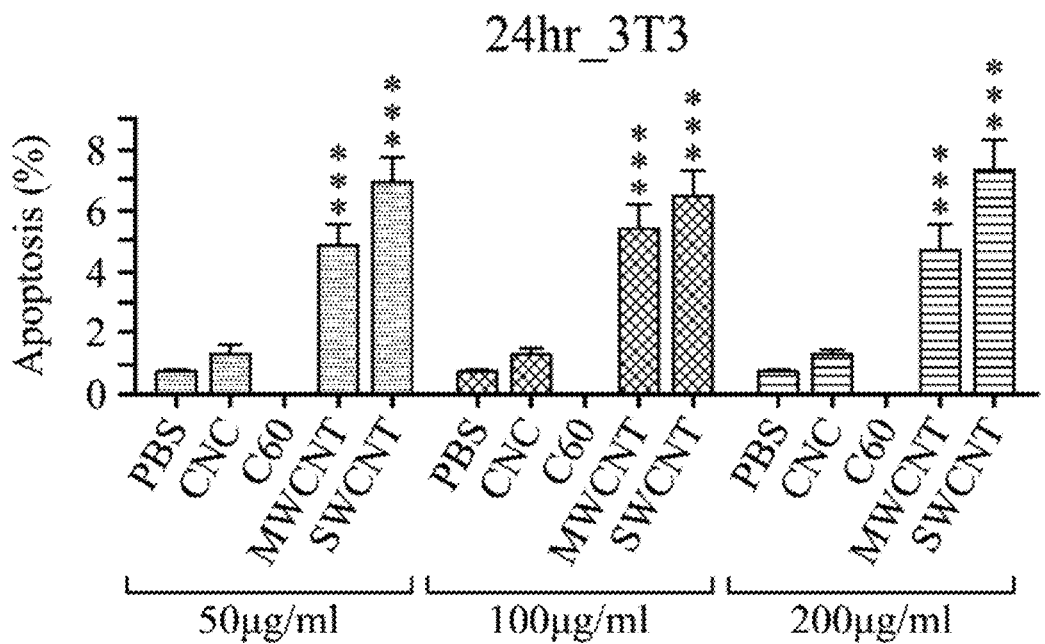
Figure 3B:
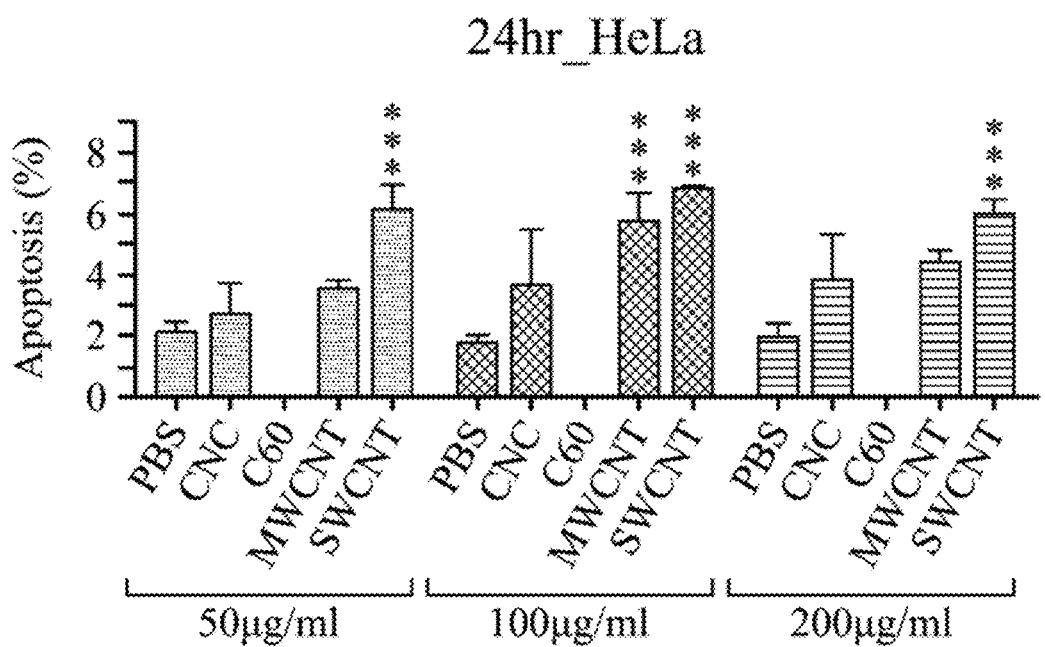
Figure 3C:
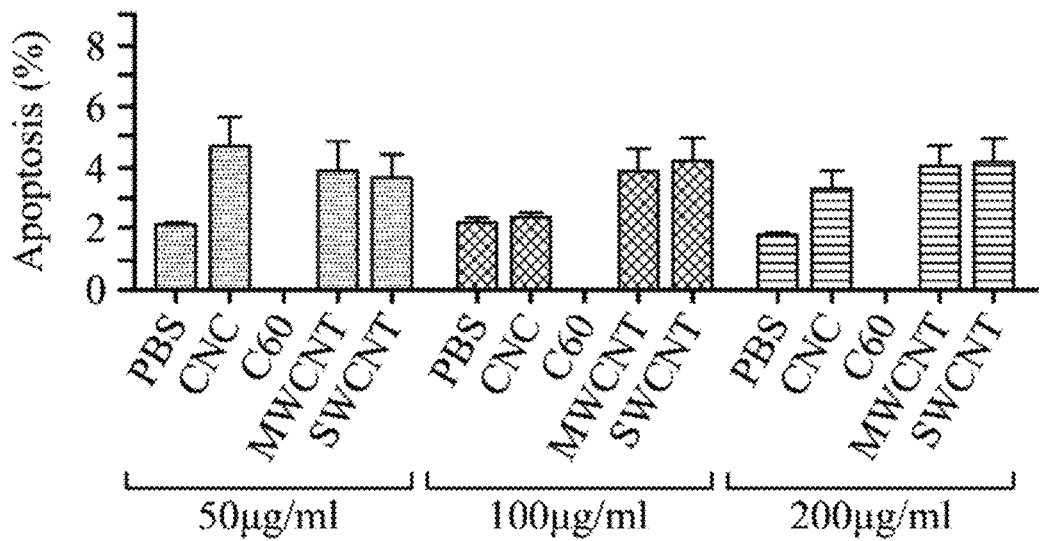
Figure 3D:
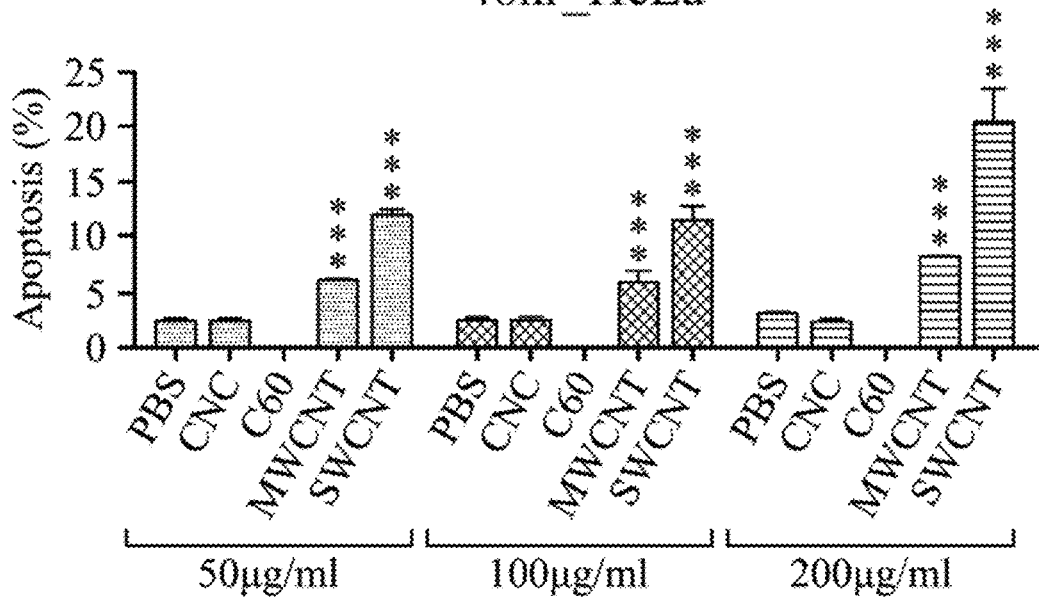
Figure 4A:
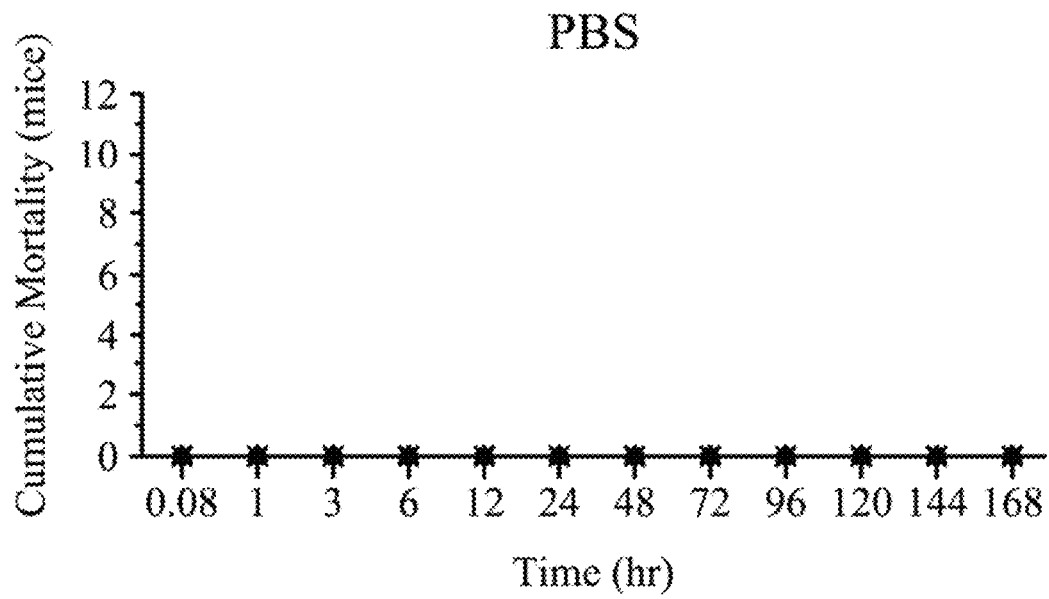
Figure 4B:
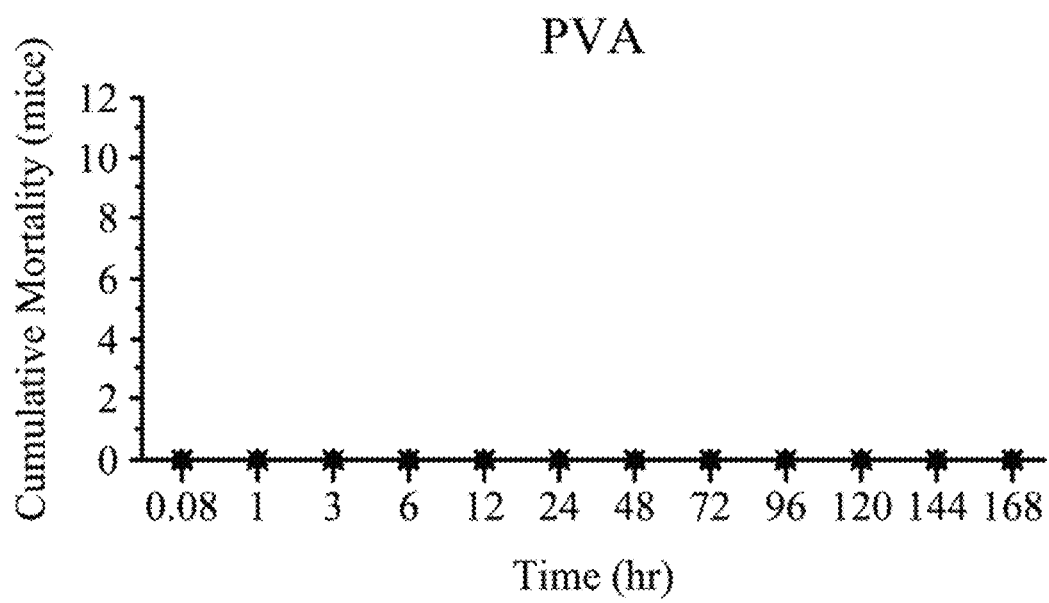
Figure 4C:
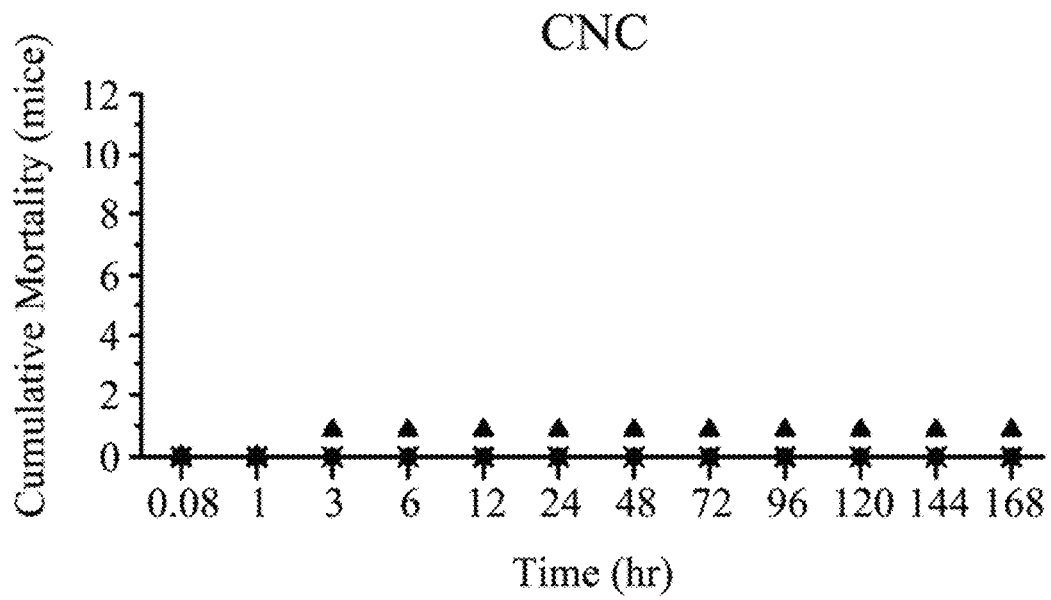
Figure 4D:
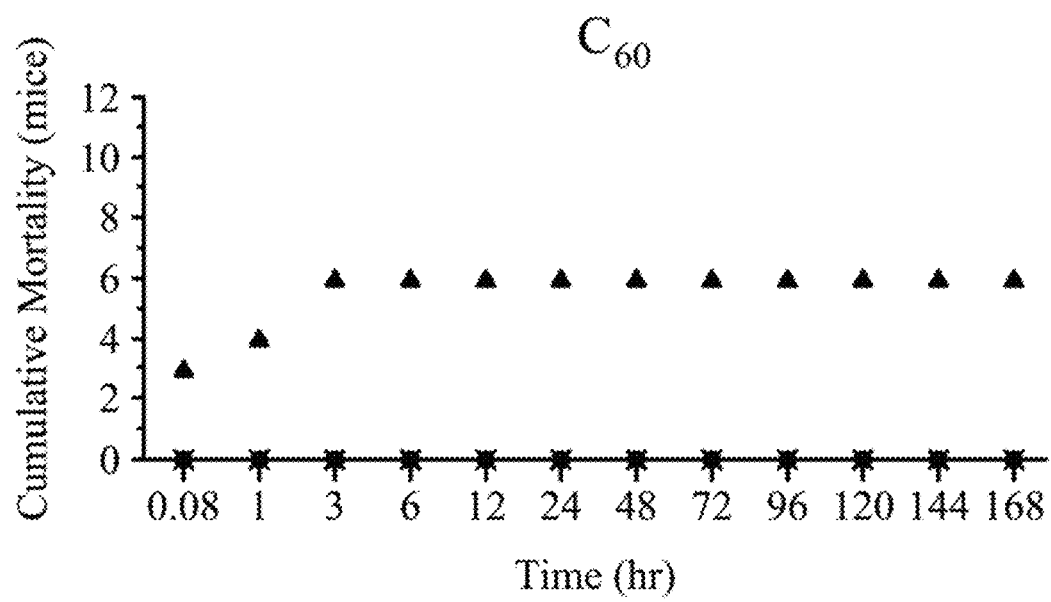
Figure 4E:
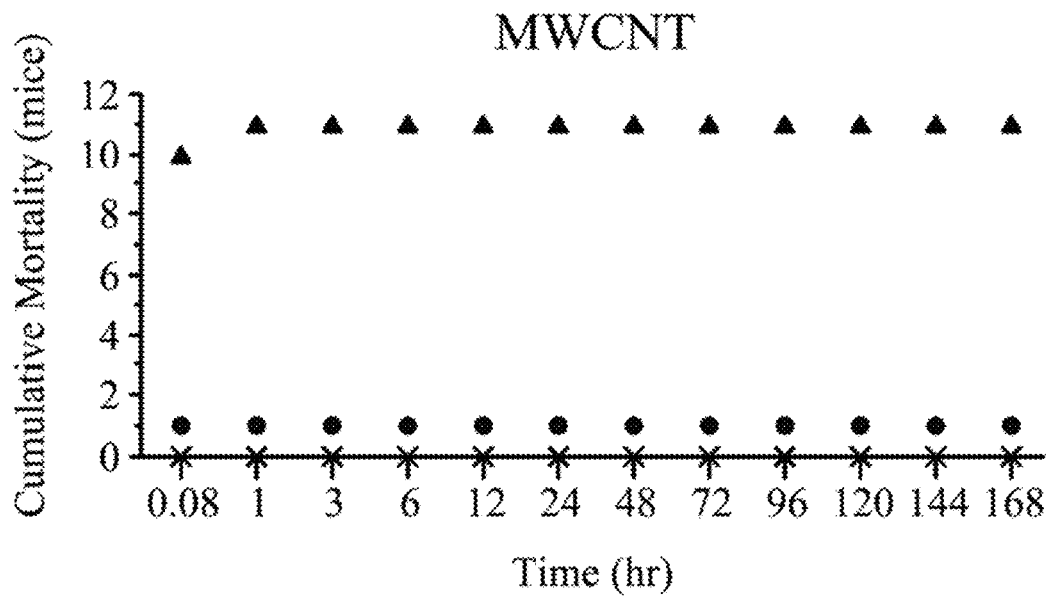
Figure 4F:
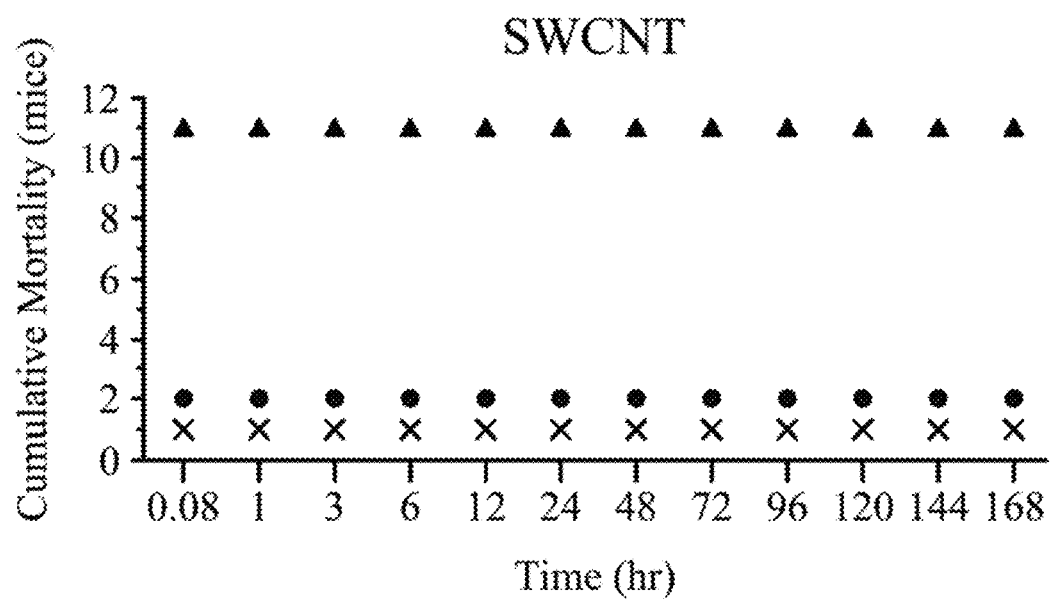

The cell apoptosis is shown in FIGS. 3A~3D. CNCs caused cell apoptosis less than other carbon materials like C60, SWCNT and MWCNT after 24 hour-culture (FIGS. 3A~3B) and 48 hour-culture (FIGS. 3C~3D). Accordingly, CNCs showed less cytotoxicity and better biocompatibility than other carbon materials.

Example 2

In Vivo Test for Cytotoxicity of Carbon Materials

FVB mice at 8~12 week-age were intravenously injected with 50 µg/g, 25 µg/g and 12.5 µg/g of PBS, PVA, SWCNTs in PVA, MWCNTs in PVA, CNCs in PVA and C60 in PVA, respectively. The murine cumulative mortality was determined and shown in FIGS. 4A~4F. in the figures, the triangle refers to the high-dose group (50 µg/g), the circle refers to the group dosing 25 µg/g and the cross refers to the group dosing 12.5 µg/g, (12 mice in each of the CNC-treated and C60-treated groups, and 11 mice in each of the PBS-treated, SWCNT-treated and MWCNT-treated groups). The results showed that the SWCNT-treated and MWCNT-treated groups had the highest mortality in dose dependence. No death was found in the CNC-treated group (25 µg/g). Accordingly, CNCs showed less cytotoxicity and better biocompatibility than other carbon materials.

Example 3

Remaining Carbon Materials in the Lung Tissue

Figure 5A:
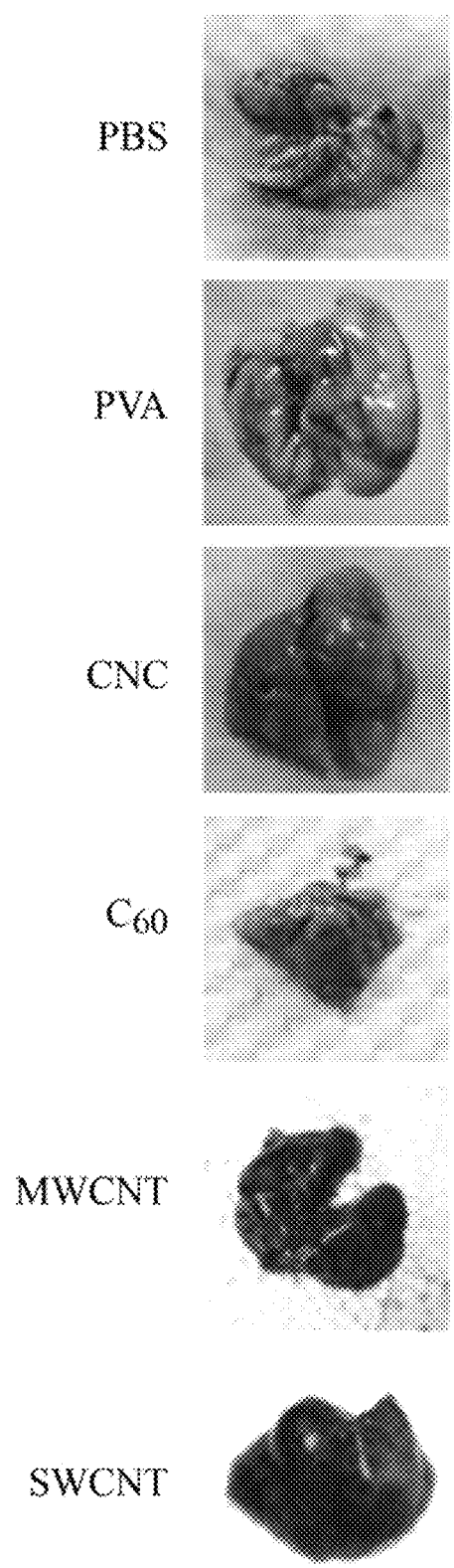
Figure 5B:
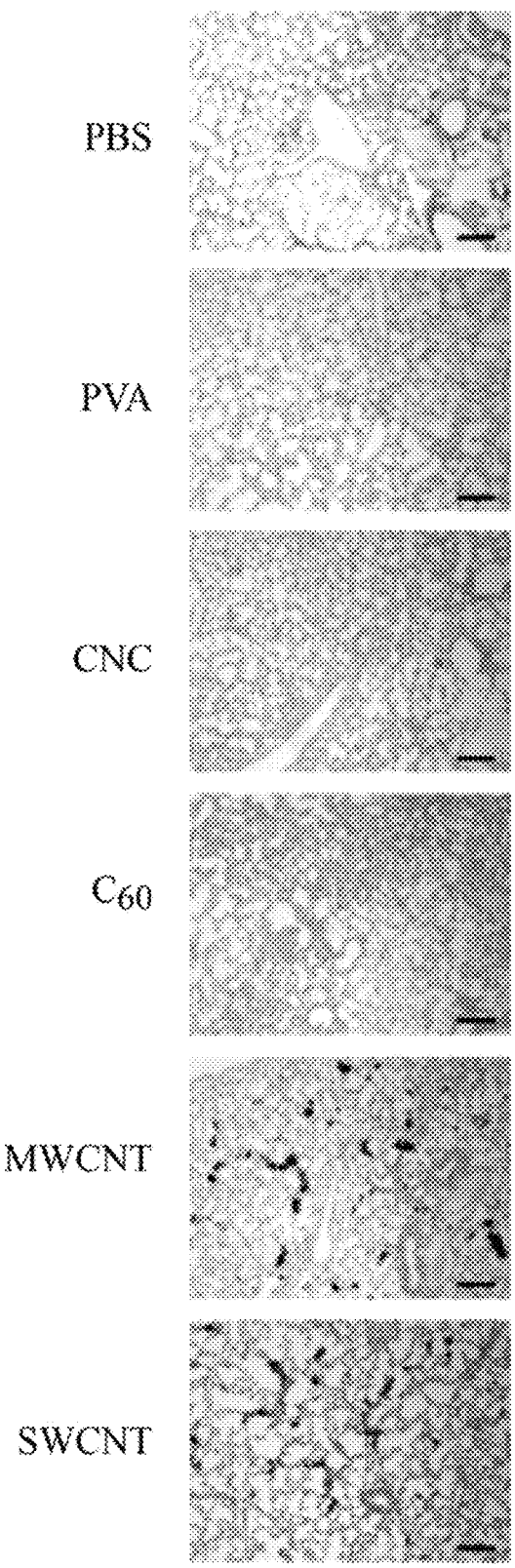

The mice were injected with 50 µg/g of PBS, PVA, SWCNTs in PVA, MWCNTs in PVA, CNCs in PVA and C60 in PVA, respectively. The lung tissue of the mice was collected after 10 minutes, and the C60-treated, SWCNT-treated and MWCNT-treated mice were dead within 10 minutes. The lung tissue and biopsy are shown as the photographs in FIGS. 5A and 5B. The remaining carbon materials in the murine lung tissue were observed. The results showed that the remaining CNCs in the lung tissue was too less to harm animals.

Example 4

Analyses for the Remaining Carbon Materials in the Lung Tissue

Figure 6A:
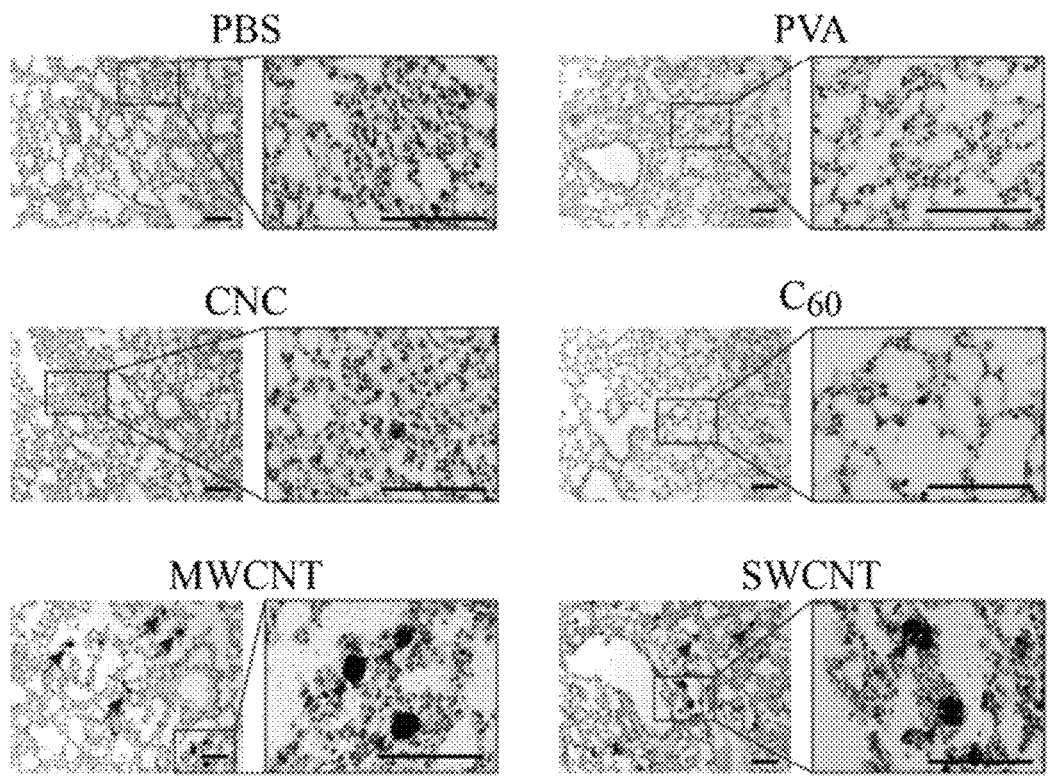
Figure 6B:
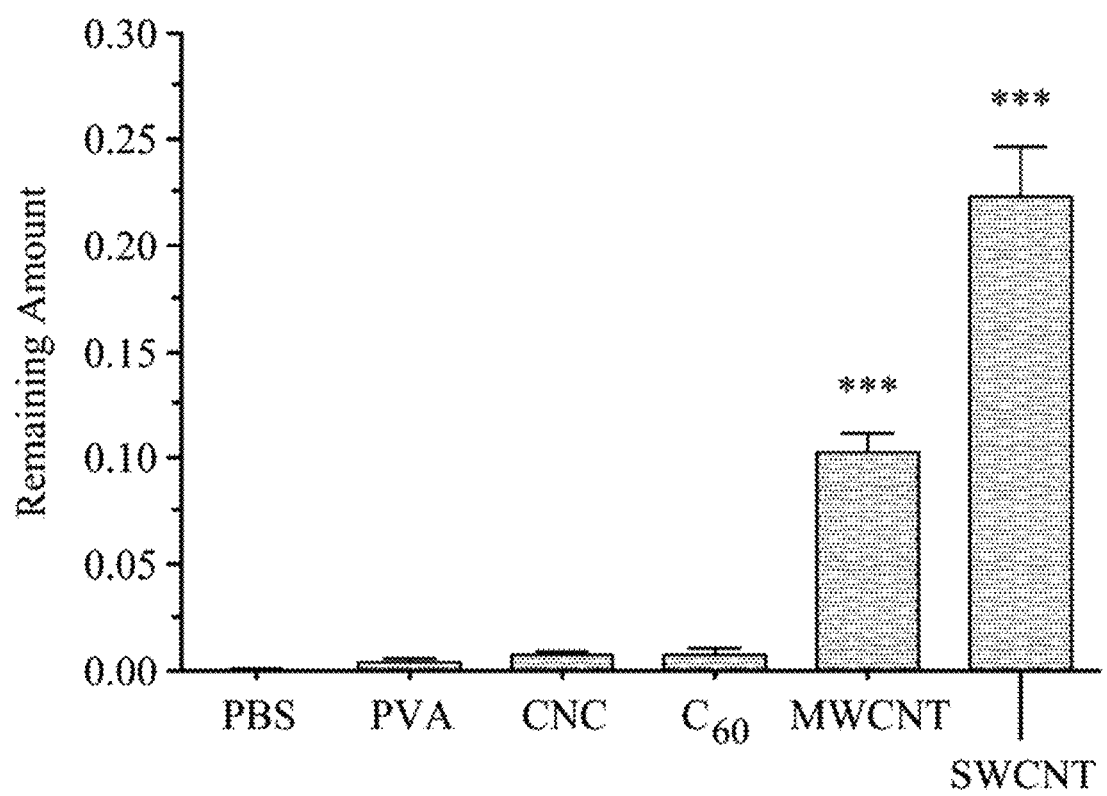

The mice were injected with 25 µg/g of PBS, PVA, SWCNTs in PVA, MWCNTs in PVA, CNCs in PVA and C60 in PVA, respectively. The lung tissue of the mice was collected after 7 days. The remaining amount of the carbon materials in the lung tissue was observed and recorded as FIGS. 6A and 6B. The scaling-up photographs in FIG. 6A showed lots of CNCs accumulated at the vessels in the lung tissue and firmed clogs. The SWCNT-treated and MWCNT-treated groups showed more remaining carbon materials in the lung tissue than the CNC-treated and C60-treated groups, The scale in FIG. 6A was 100 µm, and the mark "***" in FIG. 6B indicated p<0.0001 (based on the CNC-treated and C60-treated groups). Each group had four mice.

Example 5

Preparation of Heparin-Conjugated Carbon Nanocapsules 100 mg of carbon nanocapsules (CNCs) were added in a mixed solution of $H_2SO_4$ and $HNO_3$ at equal volumes and refluxed for two hours at the boiling temperature. Thereafter, the CNCs were collected by centrifuge and washed with distilled water. The water-soluble CNCs with surface modification of carboxyl groups were obtained.

The carboxyl-modified CNCs (0.1 mg/ml) were suspended in a citrate buffer, and 1 mg/ml of 1-ethyl-3-(3-dimethylaminopropyl)carbodiimide (EDC) solution was added. The carboxyl-modified CNCs were activated at room temperature for 1~2 hours. Thereafter, 2 IU/ml heparin sodium was added. The mixture was reacted at 4° C. overnight. The CNCs were then collected by centrifuge and washed with distilled water to remove unconjugated CNCs. The heparin-conjugated CNCs were obtained.

Example 6

Conjugation Rate of Heparin-Conjugated Carbon Nanocapsules

Figure 7:
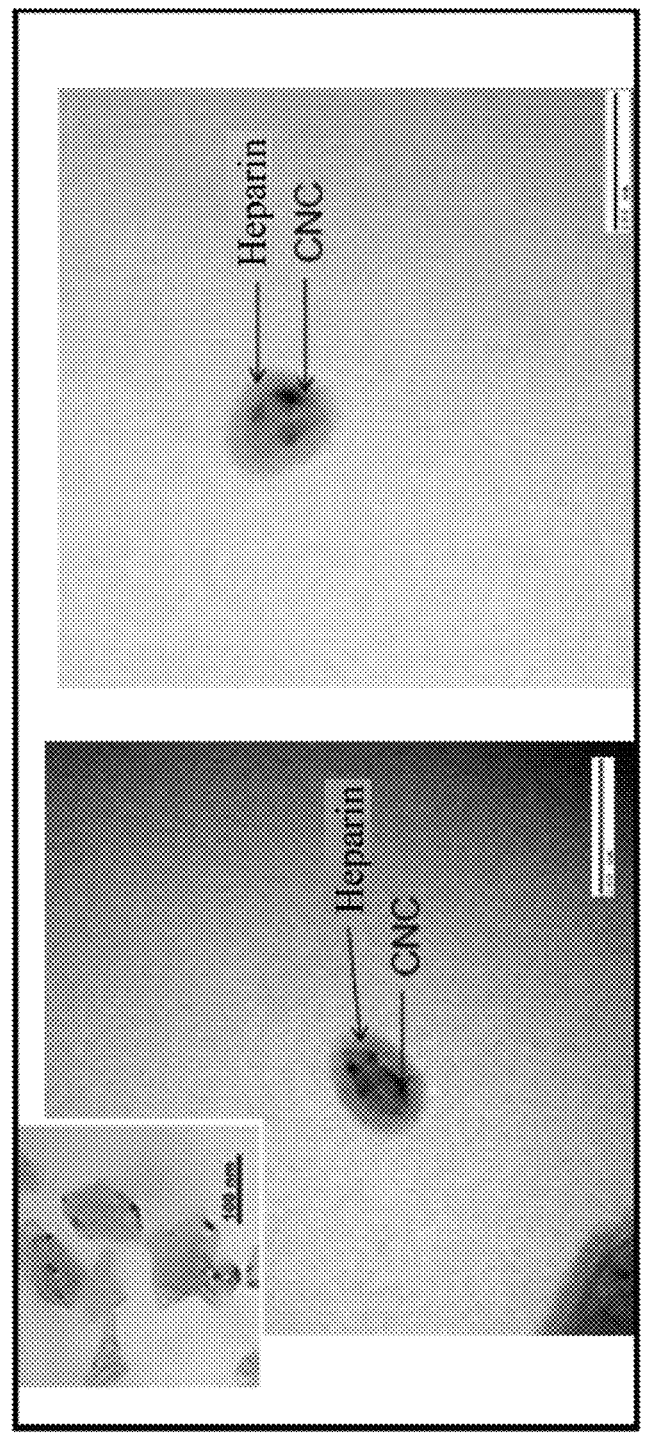
FIG. 7 is a microscopic photograph showing the heparin-conjugated carbon nanocapsule according to an exemplary embodiment.

The heparin-conjugated CNCs obtained from Example 5 were observed under a transmission electron microscope (TEM) and scan electron microscope (SEM). Under TEM, it was shown that the CNCs did not change the multiple graphite structure and the particle size after surface modification (FIG. 7). The heparin-conjugated CNCs showed a film-like coat on the surface of the carbon nanocapsules (FIG. 7).

Figure 8:
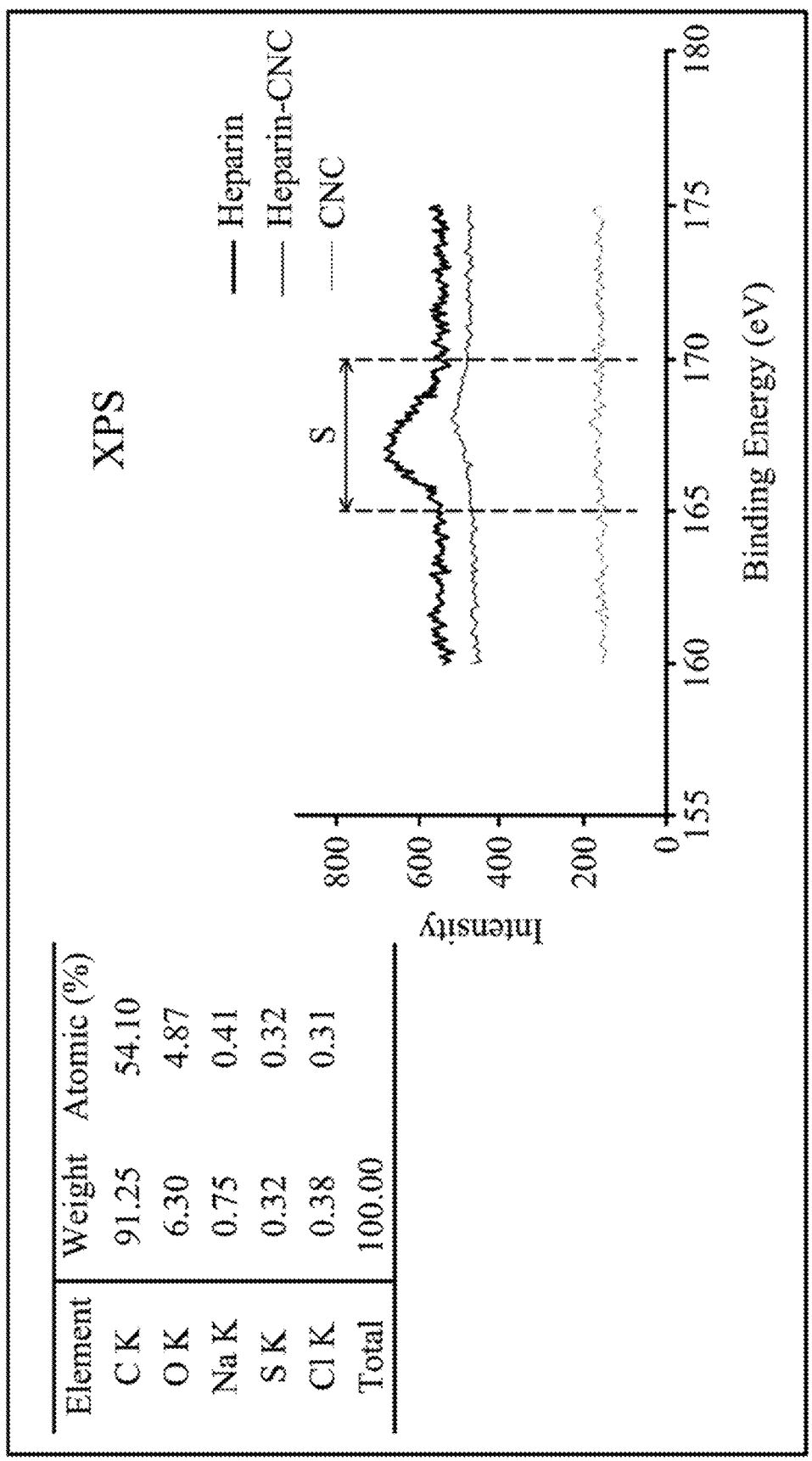
FIG. 8 shows the element analysis of the heparin-conjugated carbon nanocapsule according to an exemplary embodiment.

On the other side, the heparin-conjugated CNCs obtained from Example 5 were primarily analyzed under a high resolution X ray photoelectron spectrometer (XPS). Because heparin carried sulfur atoms, the conjugation rate of heparin on CNCs could be estimated based on the sulfur content of the conjugated CNCs. As shown in FIG. 8, the element analysis indicated that about 30% of the heparin conjugated to the CNCs.

On the other side, the conjugation efficiency of heparins on CNCs was analyzed under a Toluidine Blue O(TBO) reaction. During the reaction, the heparin-conjugated CNCs obtained from Example 5 were washed with PBS under 14,000 rpm for three times at 4° C. The supernatants were collected respectively and mixed with 0.005% TBO at a ratio of 1:4 and vibrated for 3 min. Then, an equal volume of hexane was added and mixed for another 3 min. The solution was detected at the wavelength of 631 nm. The result showed about 30% heparin conjugated to the CNCs, corresponding to the result from the XPS.

Example 7

Release Test of Heparin-Conjugated Carbon Nanocapsules

Figure 9A:
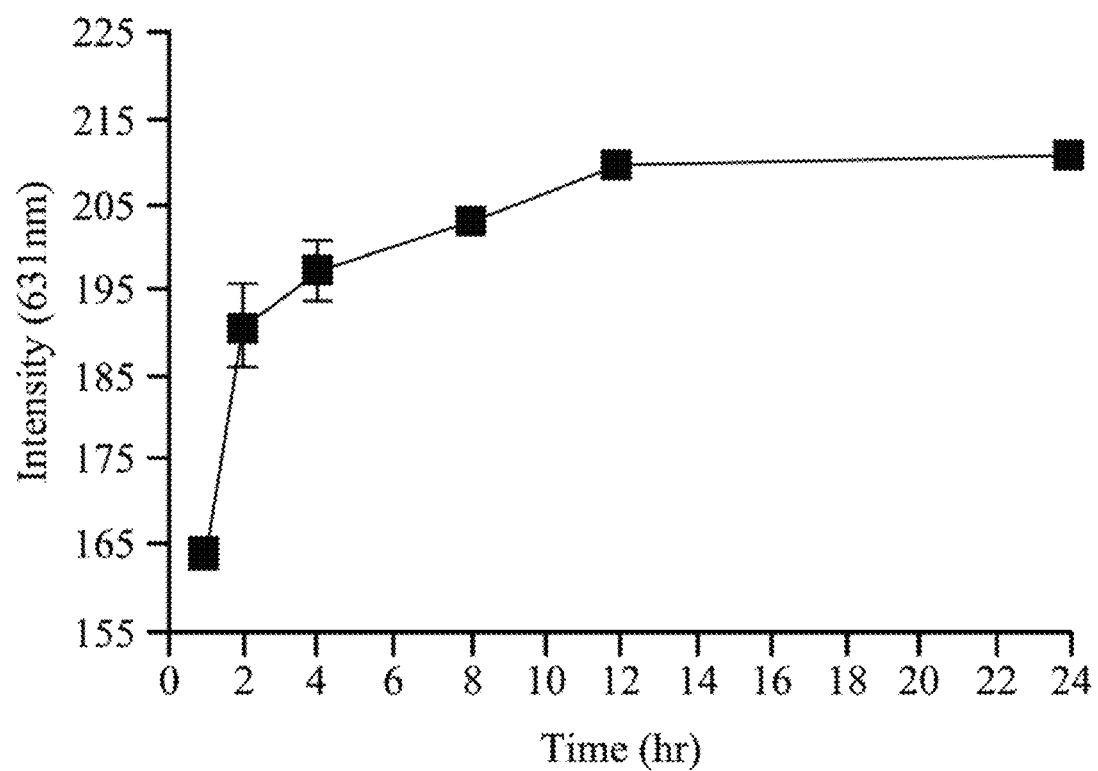
Figure 9B:
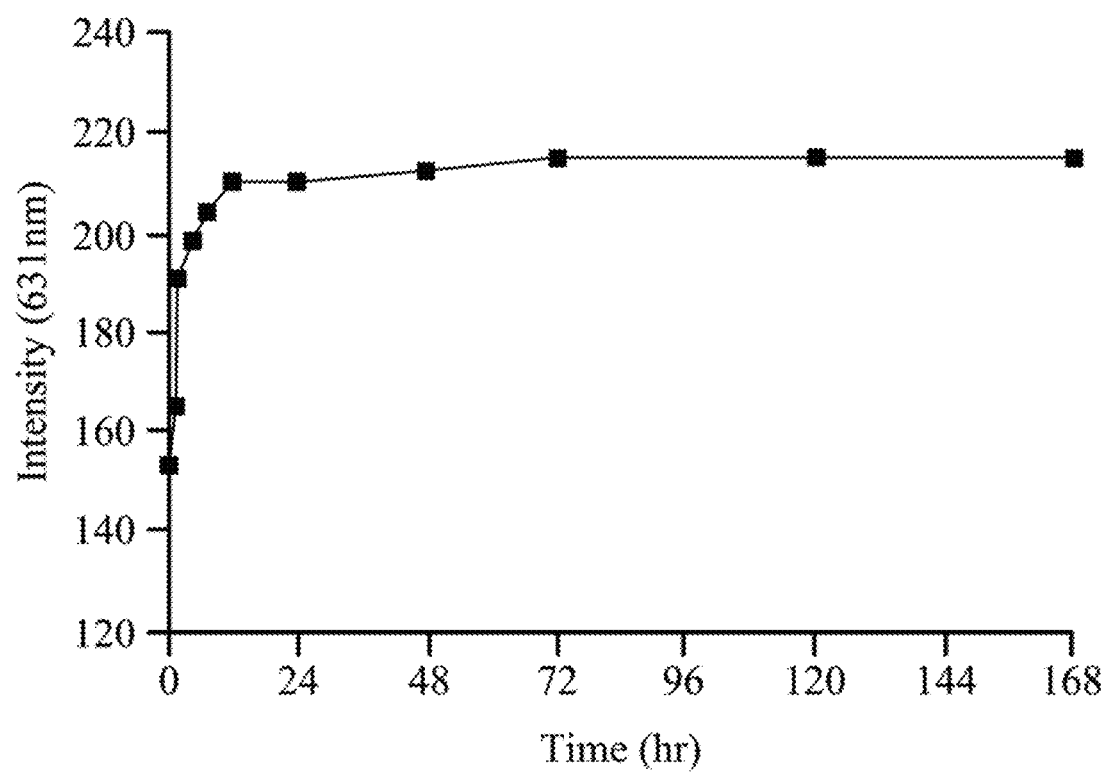

50 μg of the heparin-conjugated CNCs obtained from Example 5 were added into 1 ml PBS at 37° C. and mixed. The time was set as time 0. The mixture was then centrifuged each two hours to collect the supernatant. The concentration of heparin released in PBS was plotted as FIGS. 9A and 9B, showing that the release of heparin in PBS at 37☐ reached saturation after 12 hours.

Example 8

Anti-Coagulation of Heparin-Conjugated Carbon Nanocapsules in APTT Test

Figure 10A:
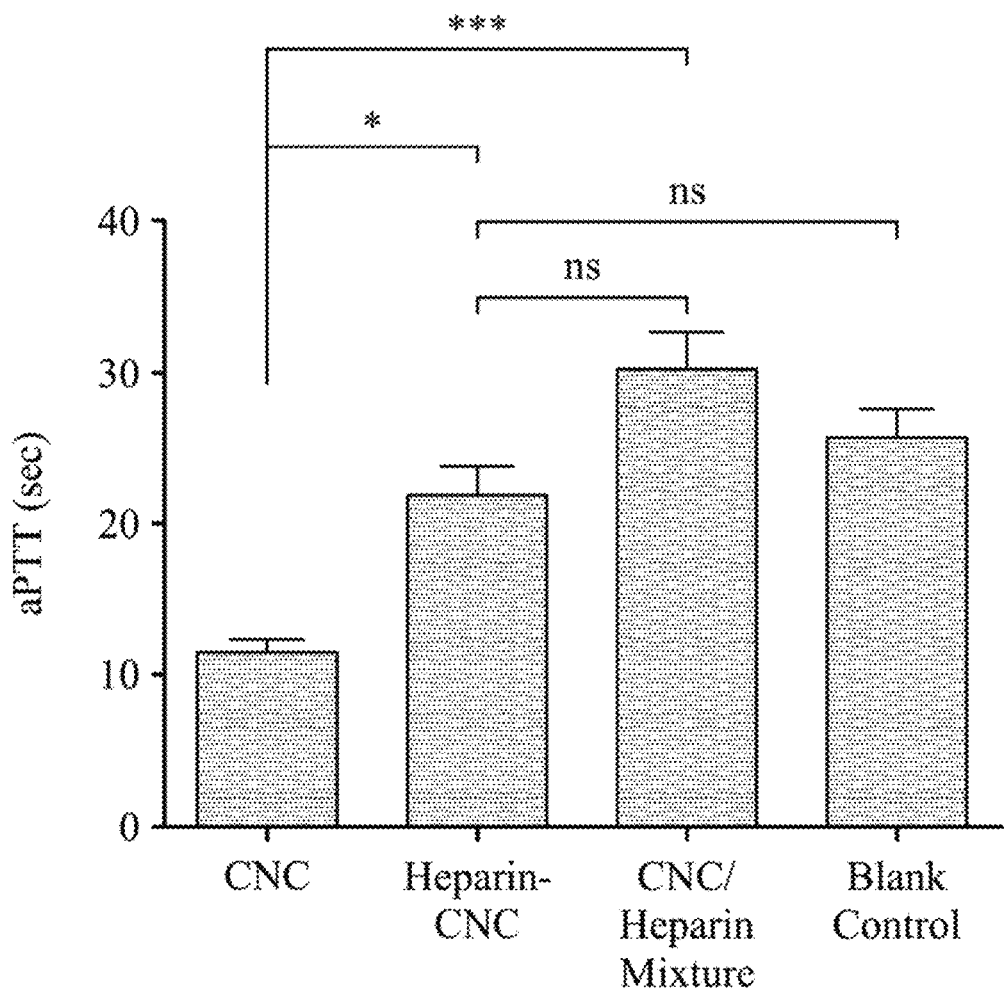
FIGS. 10A~10B show the coagulation of the heparin-conjugated carbon nanocapsule according to an exemplary embodiment by measurement of the activated partial thromboplastin tines (APTT).

In vitro: The blood from wild-type rats was added in a citrate buffer and centrifuged at 3000 g, 4° C. The serum was collected. On the other side, CNCs, heparin-conjugated CNCs and a mixture of CNCs and heparin were individually mixed with the isolated serum and the test solution Cephen-5 (liquid) for an activated partial thromboplastin time (APTT) at a ratio of 1:9:10. Incubation was at 37° C. for 3 min. Each sample was added a 0.025 μM calcium chloride and the time count started when the fibrin was present. The result showed that heparin-conjugated CNCs resulted in a prolonged time for blood clotting (thrombosis) compared to the blank control (nothing added) (FIG. 10A).

Figure 10B:
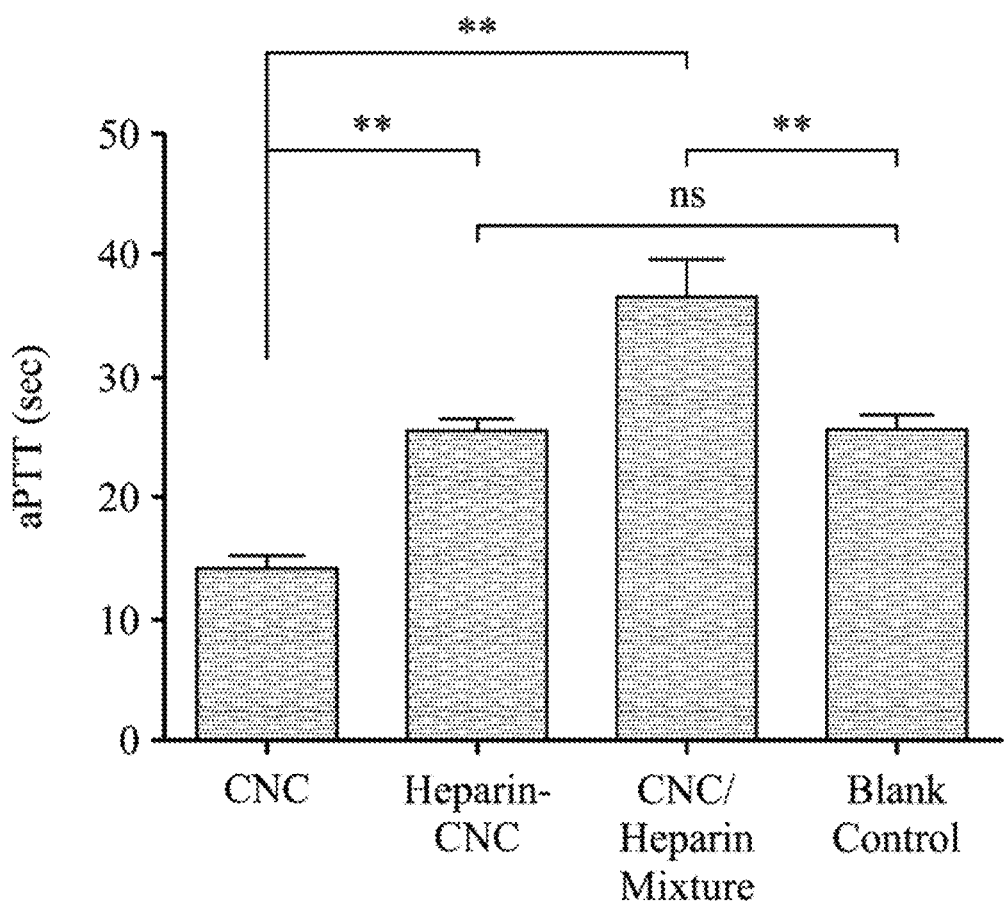

Ex vivo: Three wild-type rats in a group were intravenously injected with CNCs, heparin-conjugated CNCs and a mixture of CNCs and heparin 2 μg/g (w/w), respectively. After 10 min, the rats' blood was drawn and mixed with the test solution Cephen-5 (liquid) fur APTT at a ratio of 9:10. Incubation was at 37° C. for 3 min. Each sample was added a 0.025 μM calcium chloride and the time count started when fibrin was present. The result showed that heparin-conjugated CNCs resulted in a prolonged time for blood clotting compared to the blank control (nothing added) (FIG. 10B).

Example 9

Anti-Coagulation of Heparin-Conjugated Carbon Nanocapsules in the Ferric Chloride-Induced Thrombosis Model The model used in this example followed XinKang Wang & Lin Xu, An optimized murine model of ferric chloride-induced arterial thrombosis for thrombosis research, *Thrombosis Research* (2005) 115, 95-100 with slight modification.

Figure 11:
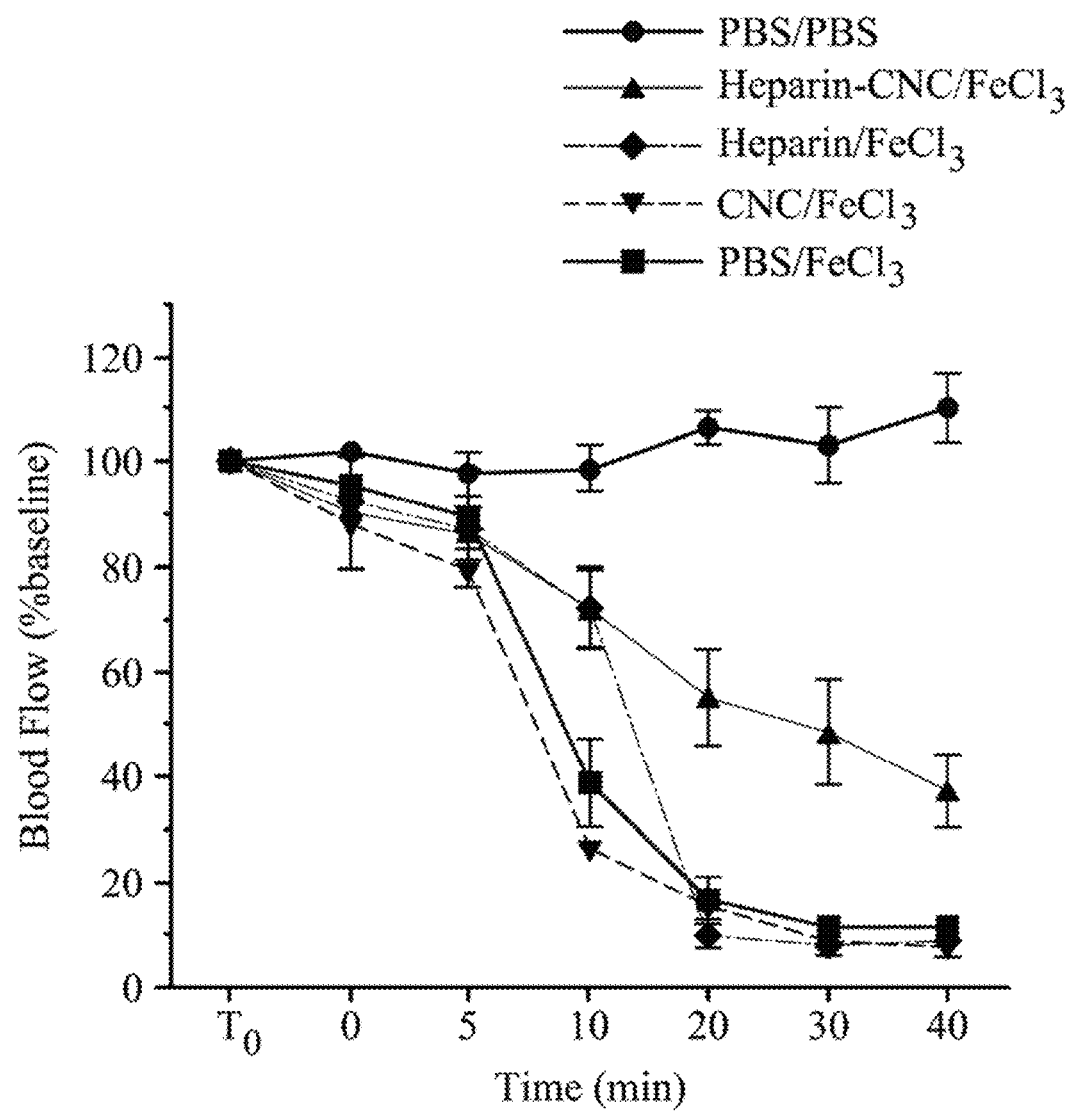
FIG. 11 shows the anticoagulation of heparin-conjugated carbon nanocapsules in a ferric chloride-induced thrombosis model according to an exemplary embodiment.

More specific, five mice in a group were intravenously injected with saline, $FeCl_3$ patch in saline, CNCs, heparin-conjugated CNCs in saline and a mixture of $FeCl_3$ patch and CNCs in saline, respectively. Doppler blood flow was measured from the injection (time 0, baseline) to 40 min after the injection. Then, the mice were sacrificed and the blood was analyzed with ELISA. The result is shown in FIG. 11.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A carbon nanocapsule conjugated with at least one of anticoagulants on a surface thereof, wherein the carbon nanocapsule is functionalized with a carboxyl group (—COOH), wherein the conjugation is via amide bond formation and the carbon nanocapsule surface conjugates with $1~10^5$ anticoagulants.

2. The carbon nanocapsule as claimed in claim 1, wherein the carbon nanocapsule has a diameter of 3~100 nm.

3. The carbon nanocapsule as claimed in claim 1, wherein the carbon nanocapsule is hollow.

4. The carbon nanocapsule as claimed in claim 1, wherein the carbon nanocapsule is filled with metals, metal oxides, metal carbides or alloys thereof.

5. The carbon nanocapsule as claimed in claim 4, wherein the metal of the metals, metal oxides, metal carbides and alloys thereof is selected from a group consisting of Sc, V, Cr, Fe, Co, Ni, Y, Zr, Mo, Ru, Pd, La, Ce, Pr, Nd, Gd, Tb, Dy, Ho, Er, Tm, Lu, Ta, Os, Ir, Pt, Au, Th and U.

6. The carbon nanocapsule as claimed in claim 1, wherein the anticoagulant comprises heparin, plasmin, serine protease, urokinase, streptokinase, warfarin, acenocoumarol, phenindione, a vitamin K antagonist, or a tissue plasminogen activator.

7. An antithrombotic agent comprising a carbon nanocapsule conjugated with at least one of anticoagulants on the surface as an active ingredient, wherein the carbon nanocapsule is functionalized with a carboxyl group (—COOH), wherein the conjugation is via amide bond formation and the carbon nanocapsule surface conjugates with $1\sim10^5$ anticoagulants.

8. The antithrombotic agent as claimed in claim 7, wherein the carbon nanocapsule has a diameter of 3~100 nm.

9. The antithrombotic agent as claimed in claim 7, wherein the carbon nanocapsule is hollow.

10. The antithrombotic agent as claimed in claim 7, wherein the carbon nanocapsule is filled with metals, metal oxides, metal carbides or alloys thereof.

11. The antithrombotic agent as claimed in claim 10, wherein the metal of the metals, metal oxides, metal carbides and alloys thereof is selected from a group consisting of Sc, V, Cr, Fe, Co, Ni, Y, Zr, Mo, Ru, Pd, La, Ce, Pr, Nd, Gd, Tb, Dy, Ho, Er, Tm, Lu, Ta, Os, Ir, Pt, Au, Th and U.

12. The antithrombotic agent as claimed in claim 7, wherein the anticoagulant comprises heparin, plasmin, serine protease, urokinase, streptokinase, warfarin, acenocoumarol, phenindione, a vitamin K antagonist, or a tissue plasminogen activator.

13. A method for preparing the anticoagulant-conjugated carbon nanocapsule as defined in claim 1, comprising:
    functionalizing a surface of the carbon nanocapsule with the carboxyl group (—COOH);
    mixing the surface-functionalized carbon nanocapsule with at least one anticoagulants; and
    isolating the anticoagulant-conjugated carbon nanocapsule.

14. The method as claimed in claim 13, wherein the carboxyl group modification is carried out by an acidic treatment.

15. The method as claimed in claim 14, wherein the acidic treatment uses hydrochloric acid, sulfite acid or a mixture thereof.

16. The method as claimed in claim 15, wherein the acidic treatment uses a mixed solution of hydrochloride acid and sulfate acid at equal volumes.

17. The method as claimed in claim 13, further adding a crosslinker in the mixing step.

18. The method as claimed in claim 17, wherein the crosslinker comprises 1-ethyl-3-(3-dimethylaminopropyl) carbodiimide or N,N'-dicylcohexyl carbodiimide.

19. The method as claimed in claim 17, further adding N-hydroxysulfosuccinimide in the mixing step.

* * * * *

UNITED STATES PATENT AND TRADEMARK OFFICE
CERTIFICATE OF CORRECTION

PATENT NO. : 8,834,932 B2
APPLICATION NO. : 13/669830
DATED : September 16, 2014
INVENTOR(S) : Patrick C. H. Hsieh et al.

Page 1 of 1

It is certified that error appears in the above-identified patent and that said Letters Patent is hereby corrected as shown below:

Title page, item (73), Assignee, change from "Industry Technology Research Institute" to
--Industrial Technology Research Institute--

Signed and Sealed this
Eleventh Day of August, 2015

Michelle K. Lee
*Director of the United States Patent and Trademark Office*